(12) United States Patent
Sotos et al.

(10) Patent No.: US 8,226,569 B2
(45) Date of Patent: Jul. 24, 2012

(54) SYSTEM AND METHOD FOR MANAGING SLEEP DISORDERS

(76) Inventors: John G. Sotos, Palo Alto, CA (US); John L. Branscum, Jr., Belmont, CA (US)

( * ) Notice: Subject to any disclaimer, the term of this patent is extended or adjusted under 35 U.S.C. 154(b) by 1489 days.

(21) Appl. No.: 11/139,294

(22) Filed: May 27, 2005

(65) Prior Publication Data

US 2006/0266356 A1    Nov. 30, 2006

Related U.S. Application Data

(60) Provisional application No. 60/574,916, filed on May 26, 2004.

(51) Int. Cl.
*A61B 5/08* (2006.01)
*A61B 7/00* (2006.01)
(52) U.S. Cl. ........................ 600/529; 600/586
(58) Field of Classification Search .................. 600/529, 600/586
See application file for complete search history.

(56) References Cited

U.S. PATENT DOCUMENTS

| | | | |
|---|---|---|---|
| 4,982,738 A | 1/1991 | Griebel | |
| 5,275,159 A | 1/1994 | Griebel | |
| 5,520,176 A | 5/1996 | Cohen | |
| 5,671,733 A | 9/1997 | Raviv | |
| 5,782,240 A | 7/1998 | Raviv | |
| 5,797,852 A | 8/1998 | Karakasoglu | |
| 5,879,313 A | 3/1999 | Raviv | |
| 5,961,447 A | 10/1999 | Raviv | |
| 5,989,193 A | 11/1999 | Sullivan | |
| 6,045,514 A | 4/2000 | Raviv | |
| 6,120,441 A | 9/2000 | Griebel | |
| 6,168,568 B1 | 1/2001 | Gavriely | |
| 6,171,258 B1 | 1/2001 | Karakasoglu | |
| 6,213,955 B1 | 4/2001 | Karakasoglu | |
| 6,223,064 B1 | 4/2001 | Lynn | |
| 6,261,238 B1 | 7/2001 | Gavriely | |
| 6,290,654 B1 | 9/2001 | Karakasoglu | |
| 6,306,088 B1 | 10/2001 | Krausman | |
| 6,375,623 B1 * | 4/2002 | Gavriely | 600/534 |
| 6,666,830 B1 | 12/2003 | Lehrman | |
| 6,811,538 B2 | 11/2004 | Westbrook | |
| 2005/0043645 A1 * | 2/2005 | Ono et al. | 600/529 |
| 2005/0113646 A1 | 5/2005 | Branscum et al. | |

OTHER PUBLICATIONS

U.S. Appl. No. 11/094,911, Sotos.
U.S. Appl. No. 11/095,154, Sotos.
AASM (American Academy of Sleep Medicine Task Force). Sleep-related breathing disorders in adults: recommendations for syndrome definition and measurement techniques in clinical research. *Sleep.* 1999;22:667-689.

(Continued)

*Primary Examiner* — Patricia Mallari

(57) ABSTRACT

The present invention provides a method for managing a patient having a sleep disorder, e.g. sleep apnea, snoring, sleep bruxism, upper airway resistance syndrome, etc. The method comprises monitoring physiological information from the patient, converting the physiological information to digital data, storing the digital data in a digital memory, identifying and characterizing epochs based on the digital data, and storing the identifying and characterizing information of the epochs in a digital memory. The method further comprises organizing the epochs according to an organization function that considers at least characterization information of the epochs, selecting an epoch based on the organizing of the epochs, and generating sound derived from the stored digital data associated with the selected epoch such that the patient hears the sound. In a specific embodiment, the physiological information monitored may include sound, e.g. respiratory sound emanating from the trachea, and/or tooth-grinding sounds.

20 Claims, 12 Drawing Sheets

| Subject | Study Time | Study Duration |
|---|---|---|
| Jim Smith | Aug. 1, 2002 11:21 pm PDT through Aug. 2, 2002 07:25 am PDT | 8 hr 4 min 33 sec |

Epoch Summary -- by Category

| Category | # Epochs | Total Duration | Audio |
|---|---|---|---|
| Quiet Breathing | 52 | 3 hr 56 min 08 sec | [Play Example] |
| Apnea | 23 | 7 min 20 sec | [Play Example] |
| Hypopnea | 115 | 24 min 17 sec | [Play Example] |
| RERA | 16 | 4 min 48 sec | [Play Example] |
| Simple Snoring | 27 | 3 hr 11 min 31 sec | [Play Example] |
| Lost Signal | 0 | — | [Play Example] |
| Non-recording | 1 | 20 min 29 sec | [Play Example] |
| Talking | 0 | — | [Play Example] |
| Total for All Categories | 234 | 8 hr 04 min 33 sec | [Play Example] |

[Playback Next Epoch]

OTHER PUBLICATIONS

A. Bar, et al. Evaluation of a portable device based on peripheral arterial tone for unattended home sleep studies. *Chest.* 2003;123:695-703.

R.C. Beckerman, et al. Tracheal breath sounds for detection of apnea in infants and children. *Critical Care Medicine.* 1982;10:363-366.

Comfortacrylics.com. Remmers sleep recorder, How to set up and use. Downloaded 2 pages on Oct. 31, 2003 from: www.comfortacrylics.com/appliance/resource/protocols/Remmers_instructions.pdf.

J. Cummiskey, et al. The detection and quantification of sleep apnea by tracheal sound recordings. *Am Rev Respir Dis.* 1982;126:221-224.

N.J. Douglas. Home diagnosis of the obstructive sleep apnoea/hypopnoea syndrome. *Sleep Med Rev.* 2003;7:53-9.

K.A. East, T.D. East. Computerized acoustic detection of obstructive apnea. *Comput Meth Prog Biomedicine.* 1985;21:213-220.

R. Ferber, et al. Portable Recording in the Assessment of Obstructive Sleep Apnea. *Sleep.* 1994;17:378-392.

J.H. Ficker, et al. Evaluation of a portable recording device (Somnocheck) for use in patients with suspected obstructive sleep apnoea. *Respiration.* 2001;68:307-12.

W.W. Flemons. Home diagnosis of sleep apnea: a systematic review of the literature: an evidence review cosponsored by the American Academy of Sleep Medicine, the American College of Chest Physicians, and the American Thoracic Society. *Chest.* 2003;124:1543-79 and 14 pages of supplementary material published online.

C.J. Griffiths, et al. A video system for investigating breathing disorders during sleep. *Thorax.* 1991;46:136-140.

L. Grote, et. al. Therapy with nCPAP: incomplete elimination of sleep related breathing disorder. *Eur Resp J.* 2000;16:921-7.

J.P. Heemels, et al. Tracheal sound detector. *Med Biol Eng Comput.* 1986;24:182-185.

W. Hida, et al. Home sleep monitor for detecting apnea episodes by nasal flow and tracheal sound recordings. *Tohoku J Exp Med.* 1988;156(Suppl.):137-142.

W. Hida, et al. Prevalence of sleep apnea among Japanese industrial workers determined by a portable sleep monitoring system. *Respiration.* 1993;60:332-337.

C.J. Hoy, et. al. Can intensive support improve continuous positive airway pressure use in patients with the sleep apnea/hypopnea syndrome? *Am J Respir Crit Care Med.* 1999;159(4):1096-1100.

F.G. Issa, et al. Digital monitoring of obstructive sleep apnea using snoring sound and arterial oxygen saturation. *Sleep.* 1993;16:S32.

F.G. Issa, et al. Digital monitoring of sleep disordered breathing using snoring sound and arterial oxygen saturation. *Am Rev Respir Dis.* 1993;148:1023-1029.

P.E. Krumpe, J.M. Cummiskey. Use of laryngeal sound recordings to monitor apnea. *Am Rev Respir Dis.* 1980;122:797-801.

C.K. Li, W.W. Flemons. State of home sleep studies. *Clin Chest Med.* 2003;24:283-295.

R.R. Marsh, et al. Recorder for assessment of upper airway disorders. *Otolaryngol Head Neck Surg.* 1983;91:584-585.

N. McArdle, et. al. Long-term use of CPAP therapy for sleep apnea/hypopnea syndrome. *Am J Respir Crit Care Med.* 1999;159(4 Pt 1):1108-14.

A.W. McCombe, et al. An acoustic screening test for obstructive sleep apnea. *Clinical Otology.* 1995;20:348-351.

N. Meslier, et al. Tracheal sound recordings detect and quantify sleep apnea, hypopnea and snores. *Am Rev Respir Dis.* 1986;113:A55.

N. Meslier, et al. Validation of a suprasternal pressure transducer for apnea classification during sleep. *Sleep.* 2002;25:753-7.

A. Morielli et al. Can sleep and wakefulness be distinguished in children by cardiorespiratory and videotape recordings? *Chest.* 1996;109:680-687.

J. Peirick, J.W. Shepard Jr. Automated apnoea detection by computer: analysis of tracheal breath sounds. *Med Biol Eng Comput.* 1983;21:632-635.

T. Penzel, et al. MESAM: a heart rate and snoring recorder for detection of obstructive sleep apnea. *Sleep.* 1990;13:175-182.

W.P. Potsic. Relief of upper airway obstruction by adenotonsillectomy. *Otolaryngol Head Neck Surg.* 1986;94:476-480.

W.P. Potsic. Comparison of ploysomnography and sonography for assessing regularity of respiration during sleep in adenotonsillar hypertrophy. *Laryngoscope.* 1987;97:1430-1437.

S.D. Ross, et al. Systematic review and meta-analysis of the literature regarding the diagnosis of sleep apnea. *Sleep.* 2000;23:519-532.

Sagatech.ca. Remmers Sleep Recorder (Formerly known as SnoreSat(TM)). Downloaded 2 pages on Mar. 22, 2005 from: http://www.sagatech.ca/products/index.html.

A. Sanna, et al. Interet su suivi des bruits respiratoires tracheaux dans le diagnostic de dysrythmies respiratoires nocturnes. *Acta Clinica Belgica.* 1991;46:159-164.

M.S. Schechter, et al. Technical report: diagnosis and management of childhood obstructive sleep apnea syndrome. *Pediatrics.* Apr. 2002; 109(4): e69.

Y. Sivan, et al. Screening obstructive sleep apnoea syndrome by home videotape recording in children. *Eur Respir J.* 1996;9:2127-2131.

Sleep Solutions Inc. NovaSom QSG Technology Summary. Downloaded 11 pages on Jul. 21, 2002 from: http://www.sleep-solutions.com/phys/phys_novasom_qsq.htm.

L.A. Smolley, D.F. Bruce. *The Snoring Cure: Simple Steps to Getting a Good Night's Sleep.* New York: Berkley Books, 1999/2000.

SNAP Laboratories LLC. Downloaded 3 web pages on Jul. 21, 2002 from: (1) http://www.snaplab.com/home.htm (2) http://www.snaptab.com/mp_demo.htm (3) http://www.snaplab.com/mp_fact.htm.

R. Stoohs, C. Guilleminault. Investigations of an automatic screening device (MESAM) for obstructive sleep apnea. *Eur Respir J.* 1990;3:823-829.

M. Thorpy, et al. Practice Parameters for the Use of Portable Recording in the Assessment of Obstructive Sleep Apnea. *Sleep.* 1994;17:372-377.

D.L. Van Brunt, et al. Intensity pattern of snoring sounds as a predictor for sleep-disordered breathing. *Sleep.* 1997;20:1151-1156.

J.E.S. White, et al. The use of sound recording and oxygen saturation in screening snorers for obstructive sleep apnea. *Clinical Otology.* 1994;19:218-221.

A.J. Williams, et al. A new computer program for storage and analysis of sleep study data. *FASEB Journal.* 1988;2:A1511.

R. Zozula, R. Rosen. Compliance with continuous positive airway pressure therapy: assessing and improving treatment outcomes. *Curr Opin Pulm Med.* 2001;7(6):391-8.

\* cited by examiner

Fig. 2A

| Subject | Study Time | Study Duration |
|---|---|---|
| Jim Smith | Aug. 1, 2002 11:21 pm PDT through Aug. 2, 2002 07:25 am PDT | 8 hr 4 min 33 sec |

Epoch Summary -- by Category

| Category | # Epochs | Total Duration | Audio |
|---|---|---|---|
| Quiet Breathing | 52 | 3 hr 56 min 08 sec | Play Example |
| Apnea | 23 | 7 min 20 sec | Play Example |
| Hypopnea | 115 | 24 min 17 sec | Play Example |
| RERA | 16 | 4 min 48 sec | Play Example |
| Simple Snoring | 27 | 3 hr 11 min 31 sec | Play Example |
| Lost Signal | 0 | -- | Play Example |
| Non-recording | 1 | 20 min 29 sec | Play Example |
| Talking | 0 | -- | Play Example |
| Total for All Categories | 234 | 8 hr 04 min 33 sec | Play Example |

Playback Next Epoch

Fig. 2B

| Subject | Study Time | Study Duration |
|---|---|---|
| Jim Smith | Aug. 1, 2002 11:21 pm PDT through Aug. 2, 2002 07:25 am PDT | 8 hr 4 min 33 sec |

Summary of "Apnea" Epochs 1-5 || 6-10 || 11-15 || 16-20 || 21-23 || All

Listed by Start Time

| Audio | Apnea # | Event # | Start Time (clock) | Start Time (elapsed) | Duration | End-Snort |
|---|---|---|---|---|---|---|
| [Playback] | 1 | 4 | 11:58 pm | 0 hr 37 min | 17 sec | No |
| [Playback] | 2 | 8 | 12:02 am | 0 hr 41 min | 12 sec | Yes |
| [Playback] | 3 | 10 | 12:06 am | 0 hr 45 min | 22 sec | No |
| [Playback] | 4 | 15 | 12:11 am | 0 hr 50 min | 14 sec | No |
| [Playback] | 5 | 63 | 1:18 am | 1 hr 57 min | 10 sec | No |

[Show Next Page]

Fig. 2C

| Subject | Study Time | Study Duration |
|---|---|---|
| Jim Smith | Aug. 1, 2002 11:21 pm PDT through Aug. 2, 2002 07:25 am PDT | 8 hr 4 min 33 sec |

Summary of "Apnea" Epochs 1-5 || 6-10 || 11-15 || 16-20 || 21-23 || All

Listed by End-Snort (Y/N)

| Audio | Apnea # | Event # | Start Time (clock) | Start Time (elapsed) | Duration | End-Snort |
|---|---|---|---|---|---|---|
| Playback | 2 | 8 | 12:02 am | 0 hr 41 min | 12 sec | Yes |
| Playback | 1 | 4 | 11:58 pm | 0 hr 37 min | 17 sec | No |
| Playback | 3 | 10 | 12:06 am | 0 hr 45 min | 22 sec | No |
| Playback | 4 | 15 | 12:11 am | 0 hr 50 min | 14 sec | No |
| Playback | 5 | 63 | 1:18 am | 1 hr 57 min | 10 sec | No |

Show Next Page

Fig. 4A

| Subject | Study Time | Study Duration |
|---|---|---|
| Jim Smith | Aug. 1, 2002 11:21 pm PDT through Aug. 2, 2002 07:25 am PDT | 8 hr 4 min 33 sec |

Highlight Reel

| 6 events |
|---|
| Duration: 2 min 07 sec |

[Playback Highlight Reel]

Fig. 4B

| Subject | Study Time | Study Duration |
|---|---|---|
| Jim Smith | Aug. 1, 2002 11:21 pm PDT through Aug. 2, 2002 07:25 am PDT | 8 hr 4 min 33 sec |

Highlight Reel

| 6 epochs -- Duration: 2 min 07 sec | | |
|---|---|---|
| # | Epoch | Audio |
| 1 | Hypopnea #4 | [Playback Epoch] |
| 2 | Snore #43-55 | [Playback Epoch] |
| 3 | Hypopnea #17 | [Playback Epoch] |
| 4 | RERA #11 | [Playback Epoch] |
| 5 | Obstructive Apnea #32 | [Playback Epoch] |
| 6 | Post-apnea hyperventilation | [Playback Epoch] |

Fig. 4C

| Subject | Study Time | Study Duration |
|---|---|---|
| Jim Smith | Aug. 1, 2002 11:21 pm PDT through Aug. 2, 2002 07:25 am PDT | 8 hr 4 min 33 sec |

Highlight Reel

| 6 epochs -- Duration: 2 min 07 sec | | |
|---|---|---|
| Status | # | Epoch |
|  | 1 | Hypopnea #4 |
|  | 2 | Snore #43-55 |
| Currently playing | 3 | Hypopnea #17 |
|  | 4 | RERA #11 |
|  | 5 | Obstructive Apnea #32 |
|  | 6 | Post-apnea hyperventilation |

[Playback Next Epoch]

SYSTEM AND METHOD FOR MANAGING SLEEP DISORDERS

CROSS-REFERENCES TO RELATED APPLICATIONS

This application claims priority to U.S. Provisional Patent No. 60/574,916 filed May 26, 2004, commonly assigned, and hereby incorporated by reference for all purposes.

BACKGROUND OF THE INVENTION

The present invention generally relates to health related disorders. More particularly, the invention provides a method and apparatus for managing behaviors related to sleep disorders. Merely by way of example, the invention is applied using digital hardware and software.

Sleep apnea is a common disorder associated with severe adverse health consequences in some patients. It is generally recognized that continuous positive airway pressure (CPAP) and other forms of positive airway pressure (PAP) can be effective treatments for the obstructive type of sleep apnea (OSA). Unfortunately, studies have found that compliance with CPAP among OSA patients is poor [L. GROTE, et. al. Therapy with nCPAP: incomplete elimination of sleep related breathing disorder. Eur Resp J. 2000; 16:921-7.] [N. McARDLE, et. al. Long-term use of CPAP therapy for sleep apnea/hypopnea syndrome. Am J Respir Crit Care Med. 1999; 159(4 Pt 1):1108-14.].

The medical profession often views non-compliance or under-compliance with advice/ecommendations from a healthcare professional as undesirable, i.e. a "negative" behavior on the part of the patient. Thus, there have been efforts to increase CPAP/PAP compliance among OSA patients. Some such efforts have, for example, employed alternate types of facemasks, humidified air, alternate pressure schedules (e.g. bi-level positive airway pressure), and the like. Compliance-enhancing efforts have also included support or behavioral-cognitive elements [C. J. HOY, et. al. Can intensive support improve continuous positive airway pressure use in patients with the sleep apnea/hypopnea syndrome? Am J Respir Crit Care Med. 1999; 159(4):1096-1100.].

In their review of CPAP compliance, Zozula and Rosen [R. ZOZULA, R. ROSEN. Compliance with continuous positive airway pressure therapy: assessing and improving treatment outcomes. Curr Opin Pulm Med. 2001; 7(6):391-8.] observe: (1) Motivational factors are strongly associated with both acceptance of the diagnosis of OSA, as well as overall treatment compliance; (2) Evidence suggests that patients' initial perception of improvement after initiating CPAP therapy is a strong predictor of subsequent treatment compliance use; (3) Successful compliance is often affected by the type and degree of patient education about the specific medical condition; (4) Initial perceptions are often decisive; therefore the timing of an intervention aiming to increase compliance is essential; (5) There is an increasing demand to find effective interventions to increase CPAP compliance.

Zozula and Rosen further note that social-psychological models are used widely to account for patient behavior change in medical settings. As one example, they summarize the "stages of change" model (usually attributed to Prochaska), in which individuals progress through predictable psychological stages in their efforts to adopt new health-related behaviors. Under the Prochaska model, a patient who transitions to a stage characterized by greater readiness to change is more apt to adopt new behaviors.

Issues of compliance and other patient behaviors are not restricted to OSA or CPAP. In general, any phase of a diagnostic or therapeutic process that requires action from a patient (or the patient's caretaker) may carry a risk of non-compliance. Some patients, for example, may delay action until convinced they have a problem. Furthermore, convincing some patients that they have a problem can be difficult, especially those unwilling to accept a physician's pronouncement of illness without accompanying proof they can understand. This difficulty may be a significant factor in many patients having a sleep disorder associated with no noticeable manifestations during or only minor noticeable manifestations wakefulness.

In the case of snoring, recording and playing back the sounds of a person's snoring have been used to prove to the person that they snore. There are limitations, however, to expanding the use of this technique for snoring and to extending this general approach to laypersons having other sleep disorders such as sleep apnea.

For example, although the sound of snoring is generally recognized correctly and readily by many laypersons, other abnormal sleep breathing events (e.g. hypopneas and respiratory effort related arousals) most likely cannot be readily and correctly recognized from their sound by the vast majority of laypersons without explanation or training. This suggests that mere audio recording and playback of sleep breathing sounds will have little influence on the behavior of an untrained lay patient who has a sleep disorder predominantly characterized by these pathological events.

An additional shortcoming arises because events associated with sleep disorders may vary in occurrence and severity during the course of a sleep period. For example, a sleeping person may snore at some times and not at others during the night. As an additional example, a sleeping person may have frequent apneas in the hours just before awakening, but not in the hours immediately after going to bed. Thus, proper characterization of a patient's sleeping may require assessment of audio recordings that span several hours of patient sleep time. Because human attention spans are generally limited, most people are unlikely to listen to such recordings for periods of hours.

From the above, it is desirable to have improved techniques for managing health related disorders. It is also desirable to have improved techniques to increase compliance with therapy and/or lead to other desired behavioral changes.

BRIEF SUMMARY OF THE INVENTION

According to the invention, techniques including a system and method for managing certain types of behaviors in patients with a sleep disorder are provided. More specifically, the invention relates to a system and method for increasing the likelihood that a patient will adopt desirable behaviors with respect to his or her sleep.

In a specific embodiment, the present invention provides a method for managing a patient having a sleep disorder, e.g. sleep apnea, snoring, sleep bruxism, upper airway resistance syndrome, etc. The method comprises monitoring physiological information from the patient, converting the physiological information to digital data, storing the digital data in a digital memory, identifying and characterizing epochs based on the digital data, and storing the identifying and characterizing information of the epochs in a digital memory. The method further comprises organizing the epochs according to an organization function that considers at least characterization information of the epochs, selecting an epoch based on the organizing of the epochs, and generating sound derived from the stored digital data associated with the selected epoch such that the patient hears the sound. In a specific embodiment, the physiological information monitored may include sound, e.g. respiratory sound emanating from the trachea, and/or tooth-grinding sounds.

Various additional objects, features, and advantages of the present invention can be more fully appreciated with reference to the detailed description and accompanying drawings that follow.

BRIEF DESCRIPTION OF THE DRAWINGS

FIGS. 2A, 2B, and 2C show web pages that reflect organization of epochs.

FIGS. 4A, 4B, and 4C show web page front ends to a highlight reel.

DESCRIPTION OF THE SPECIFIC EMBODIMENT

We have discovered that some persons who listen to selected sounds they made while sleeping will, as a result the listening, change elements of their behavior in a positive direction (i.e. behave more in line with the recommendations of a health care professional such as a physician). This discovery may be used in some cases to improve the management of patients with a sleep disorder.

We believe this phenomenon arises, at least in part, from the nature of the sounds and their emotional overtones. For example, in the case of a person with sleep apnea, respiratory sound may vanish completely or almost completely during an apnea. In the case of a person with obstructive sleep apnea, the relative quiet of an apnea may be punctuated by "struggle sounds" (we prefer the term "quackles") which sound very much like choking noises. Persons with sleep apnea may also have post-apnea hyperventilation, the sound of which can sometimes give the impression of almost-desperate attempts to catch one's breath. Similarly, in the case of sleep bruxism, the sound of teeth grinding may sometimes be distressing to a human listener.

Several sources teach the use of electronic equipment and respiratory sound in the diagnosis of sleep apnea, but fewer mention the playback of recorded sleep-breathing sounds to human ears.

Gavriely (U.S. Patent No. 6,168,568) teaches the playback of recorded breath sounds to the operator of his invention, but does not describe the playback of recorded sound to the patient. He specifically mentions, as a feature of his invention, that playback of sound from his invention may be done while the patient is acoustically isolated from the invention.

Sullivan (U.S. Pat. No. 5,989,193), Lynn and Lynn (U.S. Pat. No. 6,223,064), and Raviv and Weingarten (U.S. Pat. Nos. 5,671,733; 5,782,240; 5,879,313; 5,961,447; 6,045,514) teach listening to breathing sounds recorded from a sleeping subject, but only in the context of a physician, clinician, or operator of their respective inventions analyzing potential breathing problems of the patient. Publications in the medical literature teach playback of respiratory audio recorded from a sleeping patient, but, again, in the context of analysis; they do not mention playback to the patient or, in the case of children, to the patient's parent R. R. MARSH, et al. Recorder for assessment of upper airway disorders. Otolaryngol Head Neck Surg. 1983; 91:584-585.) (M. S. SCHECHTER, et al. Technical report: diagnosis and management of childhood obstructive sleep apnea syndrome. Pediatrics. 2002 April; 109(4):e69.)

The present disclosure teaches a method and system for using sleep sounds to influence patient behavior. It aims to provide a flexible and efficient approach to acquiring, selecting, and delivering sounds that have a high likelihood of positively impacting a patient behavior.

Figure 1:
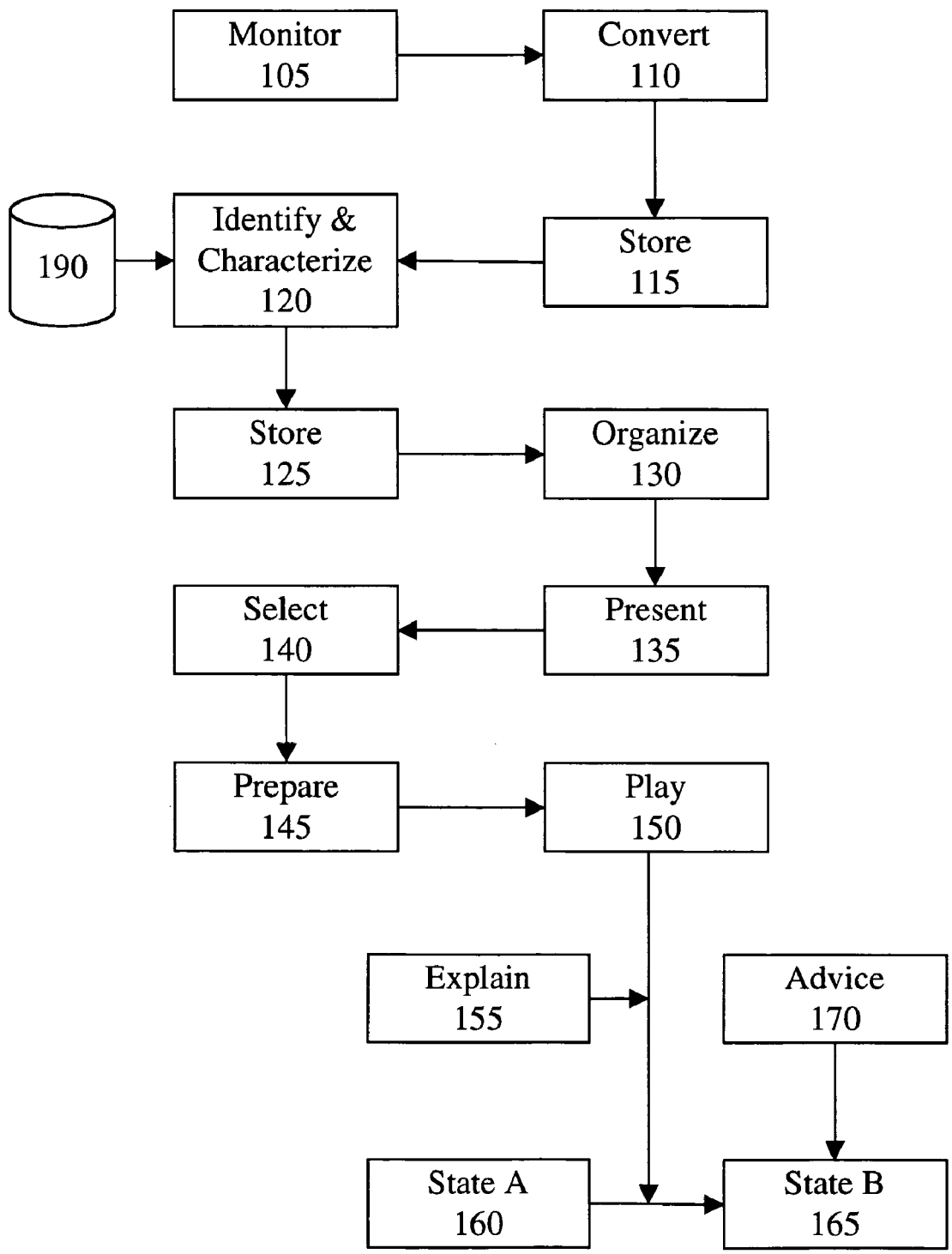
FIG. 1 shows one embodiment of a method for managing behaviors related to sleep disorders.

FIG. 1 shows one embodiment of a method for managing certain behavioral aspects of a sleep disorder in a patient. The patient may be any organism that sleeps. Certain steps depicted in FIG. 1 are amplified in later figures.

One or more physiological and/or environment parameters related to the patient are monitored 105. In cases where parameter values are in analog form, they may be converted 110 to data in digital form. For example, sound arising in the patient's airway may be picked up by a microphone and converted into corresponding digital values by an analog-to-digital converter, with or without additional processing. Persons with ordinary skill in the art will know of similar examples.

There are several possible patient parameters that may be monitored 105, including but not restricted to: electrocardiographic parameters, electroencephalographic parameters, electrooculographic parameters, myographic parameters, oximetric parameters, movement and location parameters (e.g. body position, limb movement, chest motion, abdominal motion), pressure and/or flow parameters (e.g. oronasal airflow, positive pressure delivery, esophageal pressure), gas exchange parameters (e.g. end-tidal carbon dioxide concentrations), temperature parameters, sound parameters (e.g. tracheal sound, tooth-grinding sound, musculo-skeletal sound, cardiovascular sound), parameters related to (or indicative of) arterial tone, and the like. Similarly, there are several possible environmental parameters that may be monitored 105, including but not restricted to: instrumentation-status parameters, noise (sound) parameters, ambient temperature and lighting, movement parameters, and the like. If two patients share a sleep environment, physiological parameters of the first patient may sometimes be considered as environmental parameters for the second patient.

U.S. patent application Ser. No. 10/721,115, for example, teaches a system and method for monitoring parameters related to tracheal sound, body position, arm movement, and battery voltage.

In one embodiment, some or all of the digital data are stored 115 in digital memory.

In one embodiment, epochs of data are identified and characterized 120. In this context, "identification" may refer to determining temporal boundaries that define an epoch of time, and "characterization" may refer to assigning attribute values reflecting the data associated with an epoch. For example, data obtained during a polysomnogram is often divided into 30-second epochs, i.e. each epoch normally has a start-time and also has an end-time that is 30 seconds later.

To continue the example, a state of consciousness is normally assigned to each epoch on the basis of epoch-associated polysomnographic data. (Wakefulness, stage 1 sleep, stage 2 sleep, rapid eye movement sleep, etc. are examples of states of consciousness.) Thus, in this example, each 30-second epoch can be conceptualized as having an attribute called STATE-OF-CONSCIOUSNESS and for each epoch this attribute may take the values WAKEFULNESS, STAGE-1-SLEEP, etc.

Epochs may be defined by a start time and a stop time, or, equivalently, by a start-time and a duration. Times that define an epoch may be expressed in absolute terms (e.g. as given by a clock) or in relative terms (e.g. a quantity of time before or after a reference event). In one embodiment, there is no requirement for epochs to be of uniform duration. Epochs of several durations may be present in a single patient study.

A plurality of attributes may be associated with a given epoch. We call the set of all possible attributes and attribute values for epochs the "attribute scheme." In some cases, the same information may be captured with different attribute schemes. For example, in some circumstances the two attribute schemes, A and B, below, capture approximately the same information:

| Attribute Scheme A | | Attribute Scheme B | |
|---|---|---|---|
| Attribute | Possible Values | Attributes | Possible Values |
| RESPIRATION-TYPE | APNEA, HYPOPNEA, NORMAL | APNEA HYPOPNEA NORMAL-RESPIRATION | YES, NO YES, NO YES, NO |

Different embodiments may use different attribute schemes. Merely by way of example, attribute schemes may differ when different physiological parameters are monitored. In one embodiment, epoch attributes (but not attribute values) are pre-determined and stored in memory 190.

Possible epoch attributes include, but are not restricted to:

| Attribute | Possible Values |
|---|---|
| RESPIRATION-TYPE | APNEA, HYPOPNEA, RERA, NORMAL, OTHER |
| SNORING | YES, NO, BORDERLINE |
| MOVEMENT-STATE | TRANQUIL, RESTLESS |
| ARM-MOVEMENT | YES, NO, BORDERLINE |
| BODY-POSITION | FACE-UP, FACE-RIGHT, FACE-LEFT, FACE-DOWN |
| BODY-POSITION-CHANGE | YES, NO, BORDERLINE |
| DOMINANT-FREQUENCY | numerical value, in inverse time units (e.g. Hertz) |
| SOUND-INTENSITY-MEAN | numerical value, in sound intensity units |
| SOUND-INTENSITY-VARIANCE | numerical value, in units derived from sound intensity |
| QUACKLES-PRESENT | YES, NO, INDETERMINATE |
| END-SNORT | YES, NO, INDETERMINATE |
| DESATURATION | numerical value, in desaturation percent |
| DESATURATION-SEVERITY | NONE, MILD, MODERATE, SEVERE |
| APNEA-TYPE | CENTRAL, OBSTRUCTIVE, MIXED |
| BRUXISM | YES, NO, BORDERLINE |
| TALKING | YES, NO, BORDERLINE |
| AIRWAY-RESISTANCE | numerical value, in resistance units |
| AIRWAY-HYPER-RESISTANCE-SEVERITY | NONE, MILD, MODERATE, SEVERE |
| PAP-MODE | NONE, CONTINUOUS, BILEVEL, AUTO, OTHER |
| CPAP-PRESSURE | numerical value, in pressure units (e.g. mmHg) |
| MEAN-RESPIRATION-DURATION | numerical value, in time units (e.g. seconds) |
| AROUSAL | YES, NO, BORDERLINE |

Note 1:

In this table, when the "Possible Values" entry for an attribute consists of comma-separated symbols all in capital letters, the symbols are possible values of an enumerated set. When the "Possible Values" entry is in lower case, or mixed upper and lower case letters, the entry describes possible attribute values.

Note 2:

RERA stands for "respiratory effort related arousal," a feature that has been seen in the upper airway resistance syndrome.

Some attributes may take more than one value for a given epoch, e.g. under one attribute scheme a RESPIRATION-TYPE attribute for a certain epoch could simultaneously take both the SNORING and RERA values (since both phenomena can occur simultaneously).

In one embodiment, all attributes could also take the value INDETERMINATE or UNCERTAIN. In some embodiments, a measure of certainty may be attached to attribute values. For example, a set of computer codes may classify an epoch's RESPIRATORY-TYPE as HYPOPNEA, but with only 51% "confidence" that is the correct classification. In some embodiments, epoch attribute values may have associated confidence limits, derived statistically.

In one embodiment, the duration of an epoch is not an attribute of the epoch; duration and start-time define an epoch. (Equivalently, start-time and stop-time define an epoch.)

Epochs may overlap in an embodiment. That is, a given point in time may be included within the boundaries of a plurality of epochs. For example, 20 minutes of monotonous uninterrupted snoring may be classified as one epoch, and each of the individual snoring breaths within the 20 minutes may also be classified as an epoch, and the inspiratory and expiratory phases of each breath may themselves each be an epoch. As a further example, epoch X may be defined to correspond to the period of apnea, and epoch Y may include both the period of apnea and the snort that terminates the period of apnea.

Identification and characterization of epochs 120 may include dependent sub-steps. For example, the start and end times of epoch Y (see paragraph above) can be determined with finality only when the beginning of the apneic period is known and the end of the snort is known.

Returning to FIG. 1, in one embodiment identification and characterization information produced by step 120 may be stored 125 in memory.

In one embodiment, steps 105 through 125 may proceed at least partially in parallel. For example, identification and characterization 120 of epochs associated with previously-acquired data may occur while monitoring 105 continues.

In one embodiment, organization of epochs 130 involves ranking and/or collecting epochs. In one embodiment organization 130 of epochs occurs on the basis of one or more attribute values of the epochs. Timing characteristics of an epoch may also be considered. In one embodiment organization 130 is performed by applying an organization function (not shown in FIG. 1) to epochs stored 125 in memory. Merely by way of example, an organization function may be implemented as software codes. In another embodiment, organization 130 may be performed by a human. In still another embodiment, both software codes and a human may be involved in the organization step 130.

In one embodiment, one or more epochs are presented 135 to a human in a way that reflects some or all of the results of organization 130. For example, a computer interface may display a collection of epochs having APNEA as a value for the RESPIRATION-TYPE attribute. FIGS. 2A, 2B, and 2C shows examples of web pages displaying information related to identification, characterization, and organization of epochs in a sleep study (of unspecified type) performed on a patient named "Jim Smith." FIG. 2A shows information about several categories of epochs, including the number and summed duration of all epochs within each category. ("Category" is an epoch attribute in the examples shown in FIG. 2, approximately corresponding to RESPIRATION-TYPE.) FIG. 2B shows information about a subset of epochs having the APNEA RESPIRATION-TYPE. FIG. 2C is the same as FIG. 2B, except that the epochs are sorted according to the value of epoch attribute END-SNORT (indicating whether an apnea was terminated by a snort or not). In the sleep study shown, only one apnea epoch was terminated by a snort, and so it is listed first in FIG. 2C. Presentation 135 is an optional step.

Returning to FIG. 1, one or more epochs are selected 140 for playback 150. In one embodiment, a human user makes the selection 140 in conjunction with presentation 135, e.g. using a mouse or other computer pointing device to indicate an epoch having a visible reference on an interactive computer display. In another embodiment, a set of software codes implemented on a digital computing device may perform selection 140. Selection 140 may select a collection of epochs, rather than just one epoch. In one embodiment, selection 140 may select one or more epochs.

An epoch selected in step 140 is prepared 145 for audio playback 150. Preparation 145 may employ data stored earlier (e.g. in step 115, in step 125, etc.); in cases where digital sound data were stored, such data may be retrieved and readied for conversion to (hearable) sound.

Preparation 145 assembles data associated with the selected epoch(s). For example, preparation 145 may retrieve tracheal sound data corresponding to the selected epoch(s) and convert them into a Quicktime® audio file. Preparation 145 is discussed further in connection with FIG. 5.

Playback 150 includes the actual generation of sound or other vibratory phenomena.

A human (not shown in FIG. 1) listens to the sound played back 150. The human is normally the patient, but may be a caretaker or loved one of the patient. Before hearing playback 150, the human may be conceptualized as being in a certain state A 160 with respect to his or her readiness to change one or more sleep-related behaviors. After hearing playback 150 and after receiving explanation 155 of the sound played back, the human may be conceptualized as being in state B 165 with respect to his or her readiness to change one or more sleep-related behaviors. Advice 170 to the human may further influence the human's readiness to change. In one embodiment, explanation 155 is optional.

In one embodiment "change" may include, but is not restricted to, altering, starting, and stopping. In another embodiment "behavior" may include, but is not restricted to, decisions (e.g. to undergo or decline surgery), externally visible actions, and mental actions (e.g. counting sheep as an insomniac might). In still another embodiment a "sleep-related behavior" may be a behavior that is expected to have an effect on the sleep of the patient. (Note that sleep-related behavior may occur during wakefulness).

Thus, examples of changes in sleep-related behavior include, but are not restricted to: increasing compliance with a prescribed treatment for a sleep disorder (e.g. continuous positive airway pressure, wearing of an oral appliance for the treatment of sleep bruxism or obstructive sleep apnea, sleeping with positional therapy, weight loss), increasing compliance with a preventive regimen forestalling a sleep disorder (e.g. maintaining weight, avoiding alcohol near bedtime), and deciding to accept more vigorous treatment of a sleep disorder (e.g. opting for uvulopalatopharyngoplasty as a surgical treatment for sleep apnea after failure of weight loss).

In one embodiment explanation 155 of the sound played back is brief and is delivered to the human at or near the time of playback 150. For example, after the sound of a hypopnea is played 150, the patient's physician could say to the human: "That was a near-stoppage of breathing" or, more dramatically, "That was a near choking." We have found that a short explanation is often adequate for even a lay human listener, as he or she can afterwards generally associate the sound with a past experience from life—often an experience with a significant emotional overlay (e.g. choking). There are several possible routes by which to deliver explanation 155, including, but not restricted to: orally, in print, by an animation, by a physical model, and electronically (e.g. as on a computer or telephone display).

In one embodiment advice 170 may include, but is not restricted to, a recommendation from a health care professional, or an ostensibly neutral statement of fact (e.g. "the mortality rate of the operation is 1%") that may factor into one or more changes the human is contemplating. Advice 170 may be delivered by one or more routes, as was taught for explanation 155.

Having transitioned to state B 165, the human may be confront the same or different possible changes as in state A 160.

If multiple epochs are selected 140 in one embodiment, the order of their playback 150 optionally reflects a ranking within organization 130.

Figure 6A:
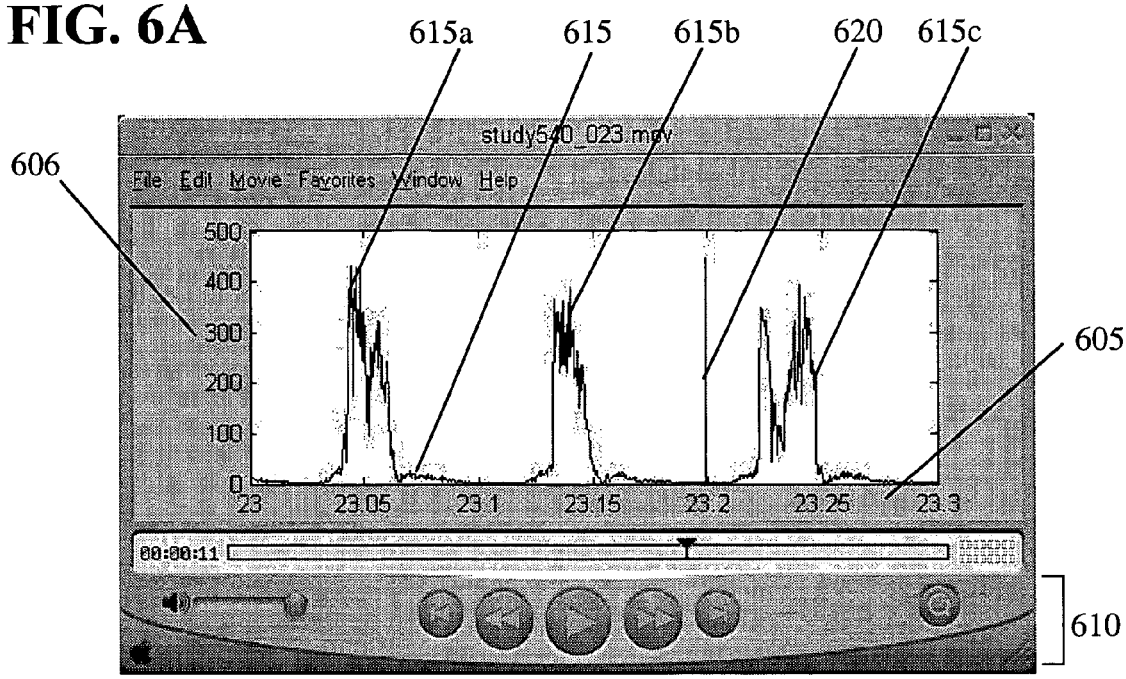
FIGS. 6A, 6B, 6C, and 6D show examples of dynamic graphical displays synchronized to audio playback.

The timing of playback 150 may be controlled in various ways. For example, the selection step 140, when performed by a human, may function to initiate preparation 145 and playback 150 soon thereafter. In another example, a separate trigger step (not shown in FIG. 1) may be employed between preparation 145 and playback 150, such that playback occurs only when the trigger step has been completed (e.g. a human user indicates he or she is ready to hear the playback). As a further example, when multiple epochs are selected 140, their associated sounds may be played back sequentially and uninterruptedly, or with a trigger step between epochs. FIG. 6A shows still another example of controlling playback 150: a computer interface with controls 610 that allow a user, among other actions, to start and pause sound playback. Other approaches are possible.

After listening to some or all sounds played back 150, the human may act in zero or more ways. For example, human 155 may deliver one or more inputs (not shown in FIG. 1) to selection step 140 and/or organization step 130. Such input(s) may specify different epochs for playback 150 or replay already-played sounds. Merely by way of example, such input(s) may occur through an interactive computer interface coupled to selection step 140 and/or organization step 130.

In one embodiment, organization 130 may involve ranking and/or collecting epochs. In such an embodiment, ranking may involve an ordering of epochs according to at least one or more attribute values, e.g. according to the value of the MEAN-SOUND-INTENSITY attribute; epochs may then be treated differently in subsequent processing depending on their rank. Collecting may involve dividing a set of epochs into subsets, e.g. according to the value of each epoch's RESPIRATION-TYPE attribute; subsets may then be treated differently in subsequent processing. Organization 130 may include both ranking and collecting, e.g. first creating collections of epochs according to their RESPIRATION-TYPE, then ranking within each collection according to MEAN-SOUND-INTENSITY.

Organization 130 is often an important step. Some patients may have hundreds of epochs of abnormal breathing during a single night, e.g. a patient having severe obstructive sleep apnea. Determining which epochs and when the epochs should be played back 150 to the human may become important in cases where (a) all epochs cannot be reasonably played back (e.g. owing to limited human attention span) and (b) playback sounds associated with different epochs have different effects on the human's readiness to change. We believe such cases are the norm.

Figure 3:
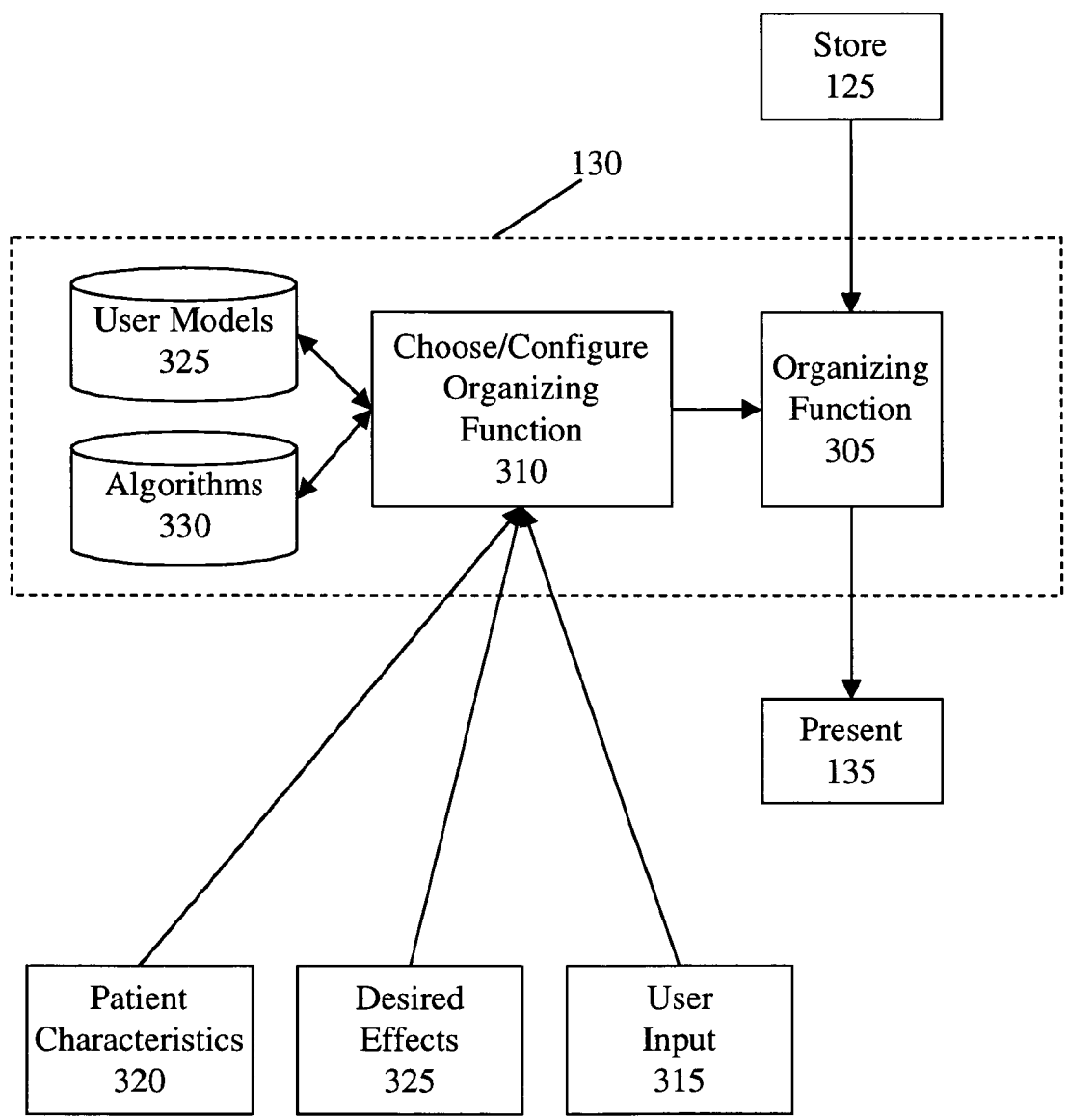
FIG. 3 shows flowchart detail of an embodiment of organizing epochs.

FIG. 3 shows an embodiment of organization step 130. In this embodiment, an organizing function 305 performs the organization of epochs. It may do so by considering attribute values associated with epochs, i.e. by ranking and/or collecting epochs based on one or more of their attribute values. Organizing function 305 may consider other information. Merely by way of example, organizing function 305 may be implemented as a set of computer codes (e.g. software). In an embodiment where a plurality of organization functions are possible, organizing function 305 should generally be chosen and/or configured 310 before use. In one embodiment, organizing function 305 may vary from invocation to invocation. Similarly, an embodiment may iteratively "evolve" an organizing function 305.

In one embodiment, choosing and/or configuring 310 organizing function 305 may be influenced by various factors. For example, choosing/configuring 310 may be performed on the basis of one or more inputs 315 from a human user (e.g. a command to select only epochs with a RESPIRATION-TYPE of APNEA), from a database of user models 325, or from a database of algorithms 330. To choose or configure items from the databases (325, 330), it is possible to use inputs 315, characteristics of the patient 320, and/or desired effects 335. Other approaches are possible. We consider constructing and configuring an organizing function 305 as equivalent.

Characteristics 320 of the patient may derive from information obtained during monitoring 105 (e.g. characterized epochs 120) or other sources (e.g. age, sex, suspected sleep disorder).

In an embodiment a "user model" is an organizing function that has been adapted for a specific listener (or group of listeners or class of listeners). Thus, a user model may relate one or more characteristics of the patient (plus/minus the human listener, if different), an effect, and one or more possible organizing functions (or templates for organizing functions). For example, one user model might represent the heuristic "If the patient has a known diagnosis of obstructive sleep apnea (OSA) and is not compliant with CPAP therapy, then organize epochs so that the most distressing epoch-sounds compatible with OSA are given the highest priority (so that the patient will be scared into complying with CPAP afterwards)." In this example, "diagnosis of OSA" and "non-compliant with CPAP" are characteristics of the patient, "prioritizing distressing sounds compatible with OSA" refers to a possible organizing function, and "complying with CPAP afterwards" refers to an effect. (All of a user model's relations need not be explicit.)

Thus, in an embodiment it is possible to choose user model(s) from database 325 that have patient characteristic(s) and/or effect(s) which match supplied patient characteristics 320 and desired effects 335. In one embodiment, user models may be implemented as software objects.

A potential advantage of embodiments of the present invention is flexibility in determining which epoch-associated sounds to playback 150. For example, separate user models may be implemented for snorers, for children, for persons in denial, for tooth-grinders, for sleep-talkers, for persons with sleep apnea, and so on. Over time, users of the invention may increase their ability to predict what types of sounds are most likely to positively affect behavior in certain classes of patients. The ability of a component of the present invention to identify and characterize epochs may be advantageous because it could spare a human operator from the potentially tedious work of listening to hours of sleep sound in order to identify the most impactful subsets.

The invention aims to allow experimentation with heuristics for organizing epochs. We have already discovered certain characteristics of impactful sounds, e.g. sounds similar to choking noises, sounds conveying a sense of abnormally high work of breathing, prolonged absence of respiratory sound, and hyperventilatory sounds after a period of absent or choking sound, among others. These sounds often carry an emotional overtone when perceived by an adult human. It is generally desirable to present such impactful sounds to a patient before the patient's attention span wanes or the patient's time with a healthcare provider ends.

We have also found that tracheal sounds are a useful source of sleep breathing sounds for playback 150. Tracheal sounds, when reproduced (to within a reasonable degree of fidelity to the original sound) through a loudspeaker or through headphones, can frequently be impactful if the patient has a sleep breathing disorder.

In one embodiment, selected epoch-associated sounds may be included in a "highlight reel" of a sleep study. The term is borrowed from sports broadcasting: a sports highlight reel normally consists of dramatic or otherwise noteworthy images, and comprises only a fraction of all images collected during a sports contest.

By analogy, an embodiment of a highlight reel for a sleep study will usually contain dramatic or noteworthy occurrences found in the playback audio associated with the sleep study. There are several possible definitions for "dramatic" and "noteworthy" in this context; such definitions may be implemented as user models or algorithms, as noted above. For example all other factors being equal, an apnea having struggle sounds is often more dramatic sounding than one that does not, a louder snore is generally more dramatic sounding than a softer snore, and so on.

In one embodiment, the contents of a highlight reel of a study is determined via one or more organization steps 130, possibly with the aid of a user model. In one embodiment the results of one or more preparation 145 steps become the highlight reel. A highlight reel may contain images in addition to sound, similar to the playback step 150.

A highlight reel may be composed automatically (e.g. by a computer), manually (e.g. by a physician), or a combination of both. For example, a human may edit or approve the contents of a highlight reel compiled or proposed by a computer.

In one embodiment the highlight reel contains epoch-related data that are anticipated to have the highest (or a significant) effect on influencing the behavior of the human that listens to (and possibly watches) the highlight reel. In many cases, the highlight reel will be relatively short when compared to the duration of the sleep study. A highlight reel offers a venue for the concentration of the most impactful sounds identified in a sleep study.

FIGS. 4A, 4B, and 4C show examples of web page frontends to the same highlight reel. The highlight reel is derived from a sleep study (of unspecified type) performed on a patient named "Jim Smith." In FIG. 4A the user may play the entire 2 minute 7 second highlight reel with the click of a single button. In FIG. 4B the web page enumerates all 6 epochs within the highlight reel and allows random-access control of playback for individual epochs. In FIG. 4C the web page enumerates all epochs within the highlight reel and allows serial-access control of playback for individual epochs.

Figure 5:
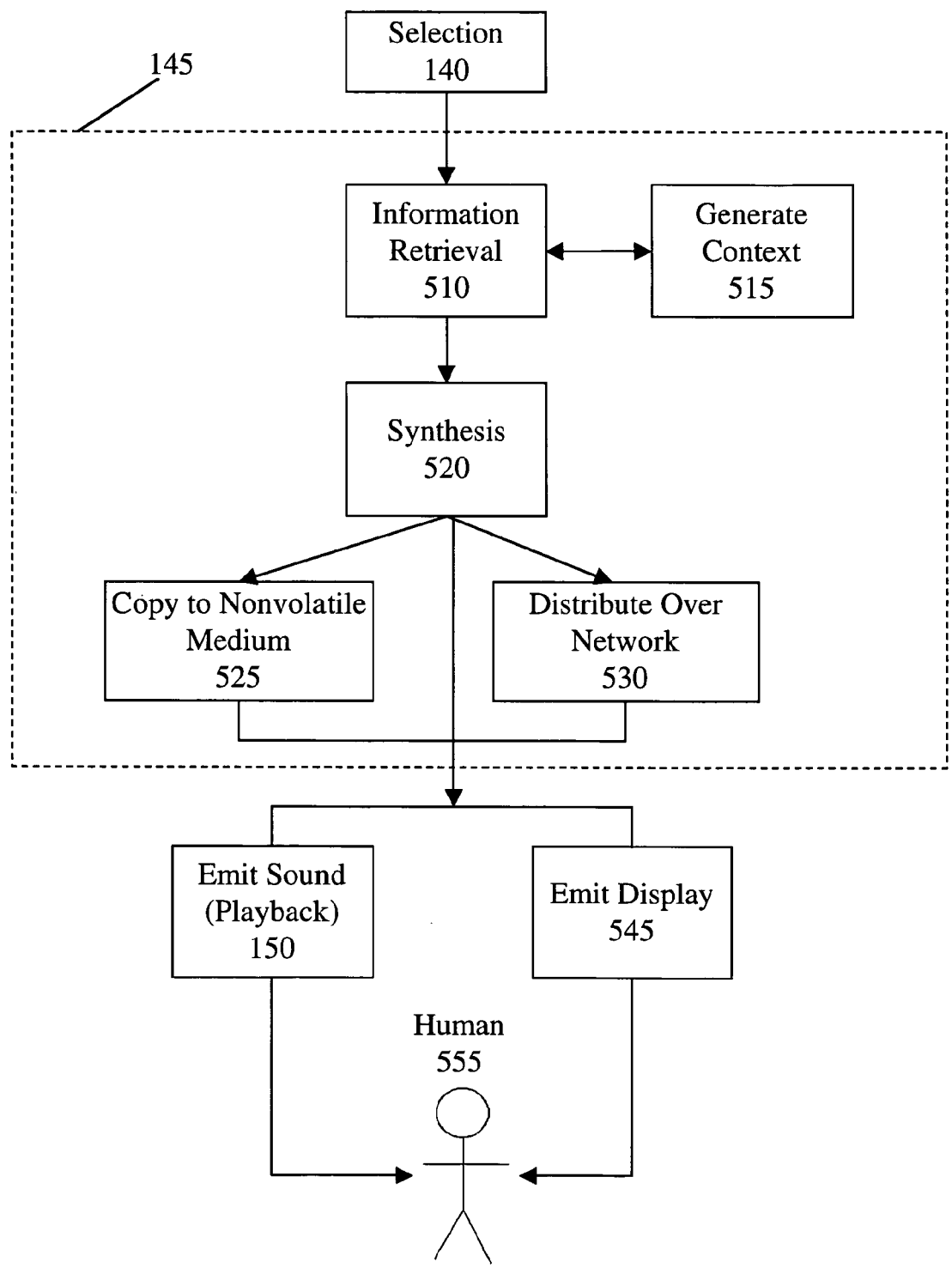
FIG. 5 shows flowchart detail of preparing data for playback.

FIG. 5 shows an embodiment of preparation step 145 in which it is decomposed into sub-steps.

After receiving a reference to an epoch from selection step 140, information retrieval step 510 may retrieve epoch-related digital data (stored in step 115) and/or epoch-related attributes and attribute values (stored in step 125).

In one embodiment, context generation 515 may occur. Here, "context" refers to those elements of an epoch's playback that are, strictly speaking, outside the temporal boundaries of the epoch. For example, if an epoch of apnea is to be played back, the audio data corresponding to that epoch may be nearly silent (because apnea can be nearly silent). A human listener may better appreciate the significance of the silence if additional sound is presented, e.g. the sound made in the few seconds before the apnea and the few seconds after the apnea. In this example, these few seconds of sound are "context" for the apnea epoch. Thus, context generation 515 is an optional step that may add additional data for playback of an epoch.

In one embodiment, synthesis 520 uses data retrieved in step 510 to create an intermediate digital representation (IDR) of the playback. The IDR contains audio data that may later be rendered into sound. For example, synthesis 520 may generate a file formatted for playback using Quicktime®, Windows Media Viewer, Real Player, Flash, or a structured vector graphics player, etc. In one embodiment, audio elements such as narration may be added to the IDR. Graphical elements may optionally be included as well. When included, certain graphical elements may optionally change appearance in synchrony with certain audio elements.

Optionally, the IDR may be copied 525 to a non-volatile medium, e.g. audio tape, hard disk, optical disk, certain MP3 players, Apple® iPod, and the like. In one embodiment, IDRs corresponding to a plurality of epochs may be so copied. In some cases, digital-to-analog conversion may occur (e.g. in copying to analog audio tape). Some persons may find it convenient to be able to transport a playable version of one or more epoch-associated playback sounds.

Optionally, the IDR may be distributed 530 over an electronic network (e.g. a local area network, the Internet, etc.), possibly in a streaming fashion.

Playback 150 takes the output of step 520 as its input. In cases where the input is in digital format, a digital-to-analog conversion will ordinarily be necessary. During playback 150 sound is emitted, possibly with an accompanying graphical display 545. We have found that sound derived from 16-bit digital sampling at 2000 Hz yields an acceptable tradeoff between storage space and fidelity.

In an embodiment where sound data were not stored in step 115, "sonification" of non-audio data may be performed as part of synthesis 520. Sonification, i.e. the conversion of non-audio data into sound, may be useful when it discloses a pattern or transient in time-varying data that is detectable by the human ear/brain system.

As one example of sonification, oxygen saturation data acquired during a sleep study may be used to modulate the frequency of an audible sound (e.g. a 440 Hz sine wave). For example, if the oxygen saturation level drops at some point, the frequency of a sine wave can be made to drop at a corresponding point. If the frequency change were above some threshold(s), a human listener would be able to hear it. Rapid variations in oxygen saturation might, therefore, be perceivable as rapid variations in the frequency of the sine wave. In one embodiment, modulation occurs at a faster rate than the sampling rate of the original data, so that long segments of data may, after sonification, occupy a shorter time. As an additional example, a library of sounds may be used for sonification, e.g. an epoch with a RESPIRATION-TYPE of HYPOPNEA could be represented acoustically by emitting a hypopnea sound of the proper duration taken from the library of sounds. These are merely examples.

In some cases, graphical displays can increase the clarity and informativeness of audio playback 150.

FIGS. 6A, 6B, 6C, and 6D show examples of graphical displays 545 associated with audio playback 150. FIG. 6A shows a window containing a Quicktime movie corresponding to an epoch of 0.3 minutes in duration. Horizontal axis 605 shows time in minutes. Standard Quicktime movie controls (e.g. rewind, play, and volume control) are at the bottom of the window in region 610. The envelope of the epoch's associated audio signal is plotted as a line 615, with vertical axis 606 showing increasing sound intensity toward the top. Three peaks in the line 615a, 615b, and 615c correspond to sounds associated with individual breaths taken by the patient. A sweep bar 620 moves from left to right across the window when the audio signal is played back 150. Its position in the window at a particular moment corresponds to the portion of the epoch's audio that is playing at that moment. Thus, the graphical display of FIG. 6A is synchronized to sound emission 150.

Figure 6B:
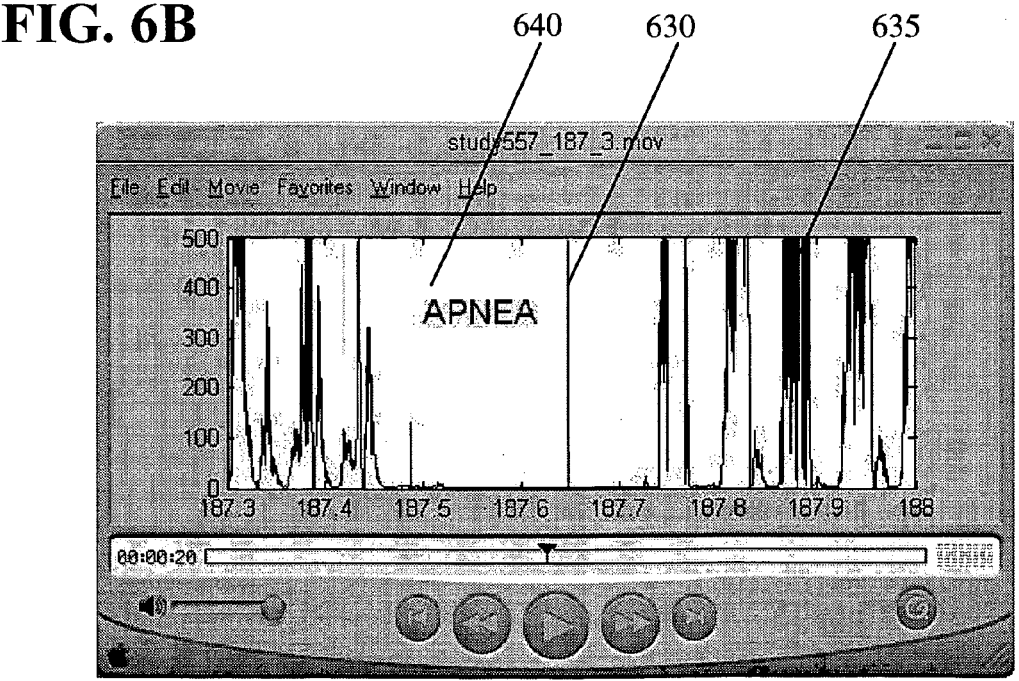

FIG. 6B is similar to FIG. 6A in showing a sweep bar 630 in a Quicktime movie window that plots the envelope 635 of an audio signal. Additionally, however, it shows an alphanumeric attribute value, "APNEA," as a legend 640 in the window. The legend is visible only during the time the sweep bar (and, therefore, audio playback) is within the time boundaries of a period of apnea. The apneic period in FIG. 6B extends from approximately minute 187.5 to 187.7 on the horizontal axis. When sweep bar 630 and audio playback 150 are at minute 187.9, for example, the APNEA legend is not visible (because the patient was not apneic at that time). A precise synchronization between graphical display and audio playback may assist humans in understanding the sounds they hear.

Figure 6C:
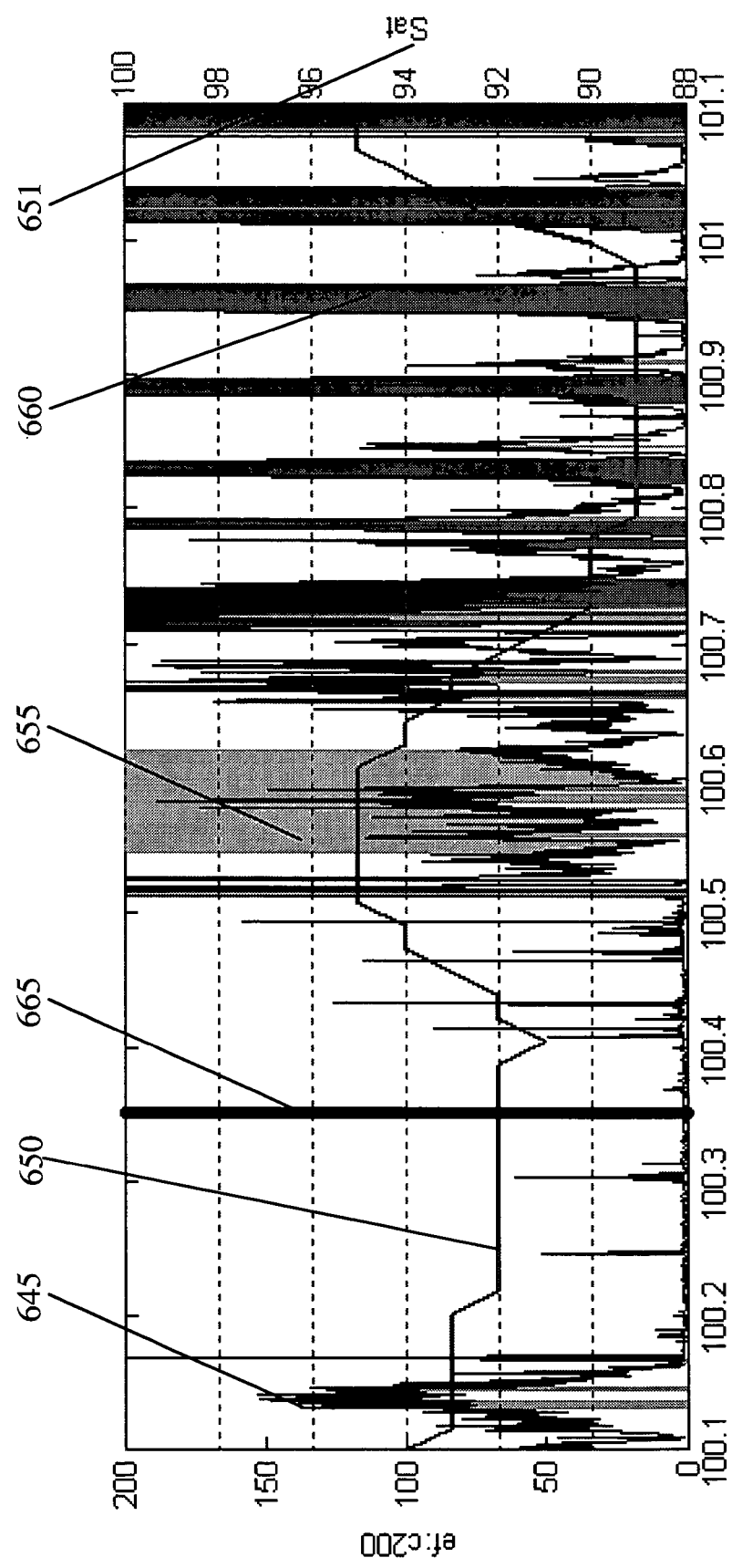

FIG. 6C illustrates a graphical display containing more than envelope and timing information. Time (in minutes) runs across the horizontal axis. The sound envelope is plotted as a blue line 645, and oxygen saturation in the patient's blood is plotted as a red line 650 (according to the vertical-axis scale 651 on the right). Arm movement of the patient is indicated by light blue shading 655 above the level of the envelope 645. Red shading 660 below the level of the envelope 645 indicates snoring sound. The sweep bar 665 is present as a vertical black line. U.S. patent application Ser. No. 11/095,154 teaches a similar approach to data visualization.

Figure 6D:
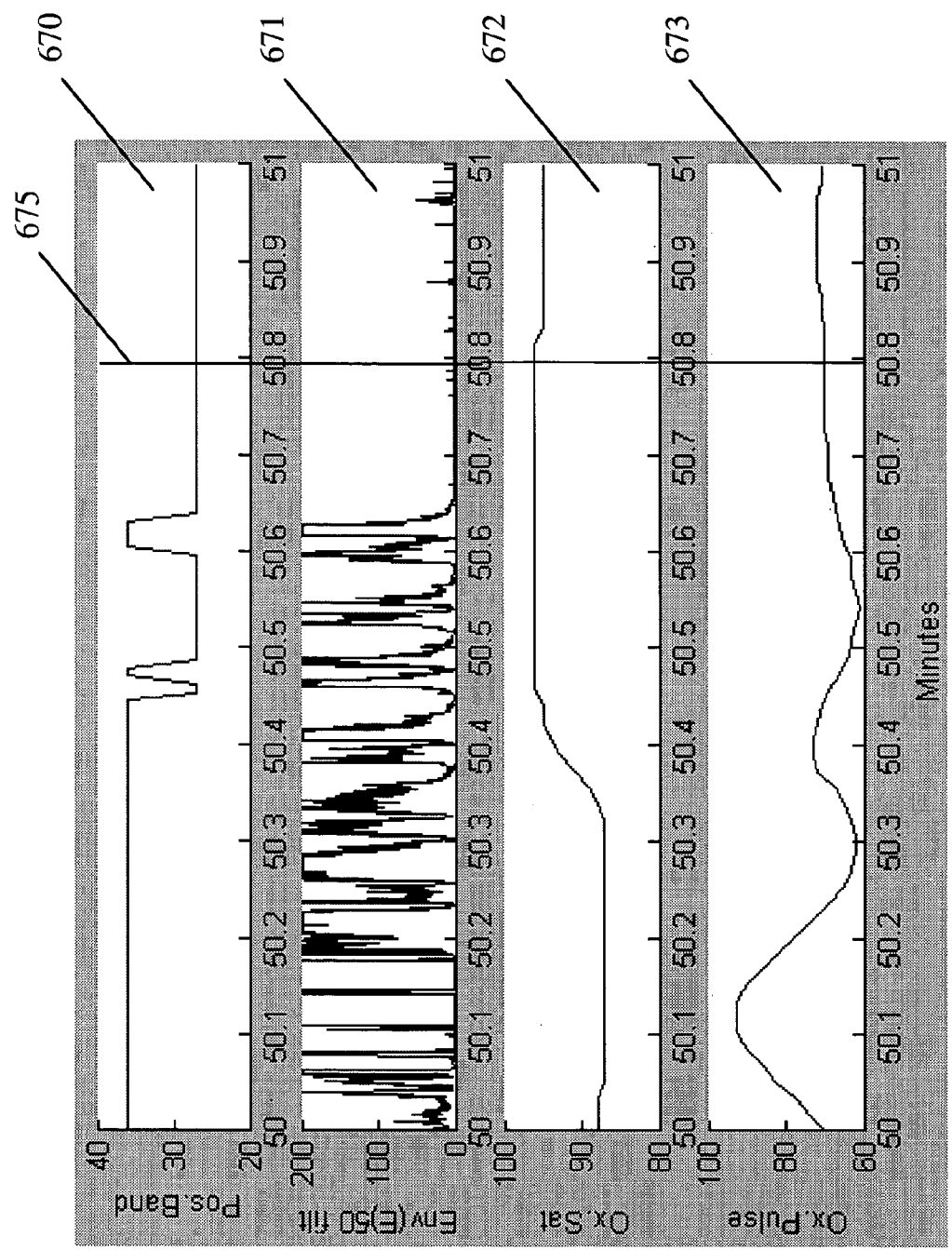

FIG. 6D shows that multiple data channels (as in FIG. 6C) can be separated into non-overlapping subplots, e.g. body position 670, sound envelope 671, oxygen saturation 672, and pulse 673. All plots have the same time (horizontal) axis, upon which the sweep bar 675 is based.

Although FIG. 6 uses a sweep bar, other interface constructs may perform similar functions.

The present invention may be applied, for example, in a standalone sleep laboratory in conjunction with polysomnography, or in cases where the patient is tested in his or her home using a portable diagnostic device. U.S. patent application Ser. No. 11/094,911 teaches a method and system compatible with the current invention.

We have discovered several potential advantages of playing back sleep-related sound as an intervention to affect a patient's behavior. These potential advantages include, but are not restricted to: (1) Timing: The intervention can be applied early in the patient's course, e.g. almost immediately upon notifying the patient of the diagnosis; (2) Simplicity: Given elements of the present invention, the intervention can be simple to perform; (3) Impact: The intervention can have a powerful impact on the patient, e.g. an emotional impact; (4) Retention: The intervention is in many cases inherently memorable; (5) Expense: It is possible to implement the intervention inexpensively in comparison with the cost of protracted teaching by health care professionals; (6) Language independence: Although the intervention will usually require some communication with the patient in a language he or she understands, the crux of the intervention is generally sounds that are independent of the patient's ability to speak a given language (e.g. the language of the health care professional interacting with the patient).

It should be noted that the above sequence of steps is merely illustrative. The steps can be performed using computer software or hardware or a combination of hardware and software. Any of the above steps can also be separated or be combined, depending upon the embodiment. In some cases, the steps can also be changed in order without limiting the scope of the invention claimed herein. One of ordinary skill in the art would recognize many other variations, modifications, and alternatives. It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for communicating information about a patient's sleep, comprising the steps of:
    capturing analog sound information spontaneously emitted by a patient during a period of time associated with a sleep period of the patient;
    converting the analog sound information into a digital form;
    storing the digital form of the analog sound information into a first memory;
    dividing a portion of the period of time associated with the sleep period into a plurality of epochs, each of the plurality of epochs having an attribute, the attribute being the same for each of the plurality of epochs;
    determining, using a computer with corresponding computer code, a value of the attribute for each of the plurality of epochs;
    selecting an epoch from the plurality of epochs in which the value of the attribute satisfies a specified criterion;
    retrieving from the first memory the digital form of the analog sound information associated with the selected epoch;
    converting the retrieved sound information into an analog form;
    outputting the analog form of the retrieved sound information to a listener.

2. The method of claim 1 wherein the attribute is predetermined and is stored in a second memory.

3. The method of claim 1 wherein the listener is the patient.

4. The method of claim 1 further comprising the step of outputting information about the value of the attribute of the selected epoch synchronously with outputting the sound.

5. The method of claim 4 wherein the step of outputting information about the value of the attribute of the selected epoch further comprises outputting information about the physiology of the patient's respiration.

6. The method of claim 5 wherein the information about the physiology of the patient's respiration includes a state selected from apnea, hypopnea, high respiratory effort, and snoring.

7. The method of claim 4 wherein the step of outputting information about the value of the attribute of the selected epoch further comprises outputting a visual representation of sound intensity.

8. The method of claim 7 wherein, at a given moment, the step of outputting information about the value of the attribute of the selected epoch further comprises outputting a visual element relating the sound being output at a given moment to the corresponding information being output at substantially the same moment.

9. The method of claim 8 wherein the sound being output and the corresponding information being output are less than 1 second apart.

10. The method of claim 1 wherein the step of dividing the plurality of epochs is based on the sound information.

11. The method of claim 3 further comprising the step of presenting information to the patient about an option to treat the condition associated with the output sound information.

12. The method of claim 1 wherein the step of selecting the epoch further comprises selecting ten or more epochs.

13. The method of claim 1 wherein sound information associated with the selected epoch is output based upon an input from the patient.

14. A method for communicating information about a patient's sleep, the method comprising the steps of:
   capturing analog sound information spontaneously emitted by a patient during a period of time associated with a sleep period of the patient;
   converting the analog sound information into a digital form;
   storing the digital form of the analog sound information into a memory;
   dividing a portion of the period of time associated with the sleep period into a plurality of epochs, each of the plurality of epochs having an attribute, the attribute being the same for each of the plurality of epochs;
   determining, using a computer with corresponding computer code, a value of the attribute for reach of the plurality of epochs;
   ranking the plurality of epochs based at least in part on the values of the attribute for the plurality of epochs;
   selecting an epoch from the plurality of epochs based on the ranking;
   retrieving from the memory the digital form of the analog sound information associated with the selected epoch;
   converting the retrieved sound information into an analog form;
   outputting the analog form of the retrieved sound information to a listener.

15. The method of claim 14 wherein the attribute is the anticipated psychological impact upon the listener of hearing the outputting of the retrieved sound.

16. The method of claim 14 wherein the listener is the patient.

17. The method of claim 14 wherein the values of the attribute for the plurality of epochs are based on a model of the listener.

18. The method of claim 17 wherein the listener is the patient.

19. The method of claim 18 wherein the model of the listener includes comorbidities of the patient.

20. The system of claim 18 wherein the model of the listener includes an estimate of the compliance of the patient with a therapy.

* * * * *